(12) United States Patent
Orban, III (10) Patent No.: US 7,445,598 B2
(45) Date of Patent: Nov. 4, 2008

(54) ENDOSCOPIC ORGAN RETRACTOR AND METHOD OF USING THE SAME

(75) Inventor: Joseph Orban, III, Norwalk, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 11 days.

(21) Appl. No.: 10/512,700

(22) PCT Filed: May 9, 2003

(86) PCT No.: PCT/US03/14773

§ 371 (c)(1),
(2), (4) Date: Oct. 26, 2004

(87) PCT Pub. No.: WO03/094744

PCT Pub. Date: Nov. 20, 2003

(65) Prior Publication Data

US 2005/0240083 A1    Oct. 27, 2005

Related U.S. Application Data

(60) Provisional application No. 60/379,327, filed on May 9, 2002.

(51) Int. Cl.
*A61B 1/32* (2006.01)
(52) U.S. Cl. .................. 600/210; 606/191; 606/194; 606/198; 604/104; 604/106; 604/107; 604/108; 600/216
(58) Field of Classification Search ............... 600/210, 600/204, 214, 219, 224, 213, 215, 216, 222, 600/225; 606/191, 194, 198; 604/104, 106, 604/107, 108
See application file for complete search history.

(56) References Cited

U.S. PATENT DOCUMENTS

| 3,831,587 | A | 8/1974 | Boyd |
| 3,857,386 | A | 12/1974 | Ashbell |
| 4,190,042 | A | 2/1980 | Sinnreich |
| 4,198,960 | A | 4/1980 | Utsugi |
| 4,744,363 | A | 5/1988 | Hasson |
| 4,950,283 | A | 8/1990 | Dzubow et al. |

(Continued)

FOREIGN PATENT DOCUMENTS

DE   35 22 649   1/1986

(Continued)

*Primary Examiner*—Cris L. Rodriguez
*Assistant Examiner*—Jonathan Werner (57) ABSTRACT

In an organ retractor including a shaft defining a longitudinal axis and a longitudinal plane, and at least one organ support assembly operatively coupled to the shaft. The organ support assembly includes a plurality of ribs having a first position, in which each of the plurality of ribs is parallel with one another, and a second position, in which a first rib of the plurality of ribs is transverse with respect to a second rib of the plurality of ribs. The at least one organ support assembly is pivotable from a first orientation, in which each of the plurality of ribs is disposed in the longitudinal plane of the shaft, to a second orientation, in which each of the plurality of ribs is disposed at an angle relative to the longitudinal plane of the shaft, and a support extending between and connected to each of the plurality of two ribs.

13 Claims, 5 Drawing Sheets

U.S. PATENT DOCUMENTS

| | | | |
|---|---|---|---|
| 5,074,840 A | 12/1991 | Yoon | |
| 5,150,706 A | 9/1992 | Cox et al. | |
| 5,163,949 A * | 11/1992 | Bonutti | 606/192 |
| 5,176,128 A | 1/1993 | Andrese | |
| 5,178,133 A | 1/1993 | Pena | |
| 5,195,505 A * | 3/1993 | Josefsen | 600/204 |
| 5,245,987 A | 9/1993 | Redmond et al. | |
| 5,250,056 A | 10/1993 | Hasson | |
| 5,261,917 A | 11/1993 | Hasson et al. | |
| 5,267,554 A | 12/1993 | Wilk | |
| 5,271,385 A | 12/1993 | Bailey | |
| 5,281,237 A | 1/1994 | Gimpelson | |
| 5,301,658 A | 4/1994 | Zhu et al. | |
| 5,318,013 A | 6/1994 | Wilk | |
| 5,337,736 A | 8/1994 | Reddy | |
| 5,339,801 A * | 8/1994 | Poloyko et al. | 600/214 |
| 5,350,391 A | 9/1994 | Iacovelli | |
| 5,351,679 A * | 10/1994 | Mayzels et al. | 600/214 |
| 5,359,995 A | 11/1994 | Sewell, Jr. | |
| 5,362,294 A | 11/1994 | Seitzinger | |
| 5,374,261 A | 12/1994 | Yoon | |
| 5,390,664 A * | 2/1995 | Redmond et al. | 600/224 |
| 5,391,180 A | 2/1995 | Tovey et al. | |
| 5,403,329 A | 4/1995 | Hinchcliffe | |
| 5,437,645 A * | 8/1995 | Urban et al. | 604/165.02 |
| 5,456,695 A | 10/1995 | Herve Dallemagne | |
| 5,470,338 A | 11/1995 | Whitfield et al. | |
| 5,474,568 A | 12/1995 | Scott | |
| 5,501,653 A | 3/1996 | Chin | |
| 5,505,689 A * | 4/1996 | Kramer et al. | 600/204 |
| 5,507,796 A | 4/1996 | Hasson | |
| 5,514,075 A * | 5/1996 | Moll et al. | 600/202 |
| 5,514,157 A * | 5/1996 | Nicholas et al. | 606/206 |
| 5,549,627 A | 8/1996 | Kieturakis | |
| 5,549,636 A | 8/1996 | Li | |
| 5,554,101 A * | 9/1996 | Matula et al. | 600/214 |
| 5,569,165 A * | 10/1996 | Chin et al. | 600/204 |
| 5,571,115 A * | 11/1996 | Nicholas | 606/119 |
| 5,573,495 A * | 11/1996 | Adler | 600/204 |
| 5,582,577 A | 12/1996 | Lund et al. | |
| 5,593,443 A | 1/1997 | Carter et al. | |
| 5,613,939 A * | 3/1997 | Failla | 600/201 |
| 5,647,836 A | 7/1997 | Blake, III et al. | |
| 5,656,012 A * | 8/1997 | Sienkiewicz | 600/204 |
| 5,662,676 A | 9/1997 | Koninckx | |
| 5,722,935 A * | 3/1998 | Christian | 600/214 |
| 5,735,289 A | 4/1998 | Pfeffer et al. | |
| 5,735,845 A | 4/1998 | Zupkas | |
| 5,746,763 A | 5/1998 | Benderev et al. | |
| 5,775,661 A | 7/1998 | Matsumoto et al. | |
| 5,785,647 A * | 7/1998 | Tompkins et al. | 600/201 |
| 5,792,042 A | 8/1998 | Cohen et al. | |
| 5,803,902 A * | 9/1998 | Sienkiewicz et al. | 600/203 |
| 5,807,243 A * | 9/1998 | Vierra et al. | 600/204 |
| 5,810,721 A | 9/1998 | Mueller et al. | |
| 5,817,973 A | 10/1998 | Elco | |
| 5,860,987 A | 1/1999 | Ratcliff et al. | |
| 5,888,196 A * | 3/1999 | Bonutti | 600/204 |
| 5,891,162 A | 4/1999 | Sugarbaker et al. | |
| 5,904,649 A | 5/1999 | Andrese | |
| 5,904,711 A | 5/1999 | Flom et al. | |
| 5,954,057 A | 9/1999 | Li | |
| 5,968,074 A | 10/1999 | Prestel | |
| 5,993,461 A | 11/1999 | Abae | |
| 6,010,447 A | 1/2000 | Kardjian | |
| 6,017,304 A * | 1/2000 | Vierra et al. | 600/204 |
| 6,027,519 A | 2/2000 | Stanford | |
| 6,039,686 A | 3/2000 | Kovac | |
| 6,042,534 A | 3/2000 | Gellman et al. | |
| 6,042,536 A | 3/2000 | Tihon et al. | |
| 6,042,596 A * | 3/2000 | Bonutti | 606/190 |
| 6,048,309 A | 4/2000 | Flom et al. | |
| 6,053,935 A * | 4/2000 | Brenneman et al. | 606/232 |
| 6,068,591 A | 5/2000 | Bruckner et al. | |
| 6,077,214 A | 6/2000 | Mortier et al. | |
| 6,090,041 A | 7/2000 | Clark et al. | |
| 6,090,043 A | 7/2000 | Austin et al. | |
| 6,110,101 A | 8/2000 | Tihon et al. | |
| 6,117,067 A | 9/2000 | Gil-Vernet | |
| 6,120,437 A * | 9/2000 | Yoon et al. | 600/204 |
| 6,142,935 A | 11/2000 | Flom et al. | |
| 6,149,583 A * | 11/2000 | Vierra et al. | 600/204 |
| 6,165,120 A | 12/2000 | Schweich, Jr. et al. | |
| 6,165,121 A | 12/2000 | Alferness | |
| 6,165,122 A | 12/2000 | Alferness | |
| 6,206,827 B1 | 3/2001 | Chin et al. | |
| 6,206,889 B1 | 3/2001 | Bennardo | |
| 6,221,005 B1 | 4/2001 | Bruckner et al. | |
| 6,221,008 B1 * | 4/2001 | Keckstein et al. | 600/204 |
| 6,245,082 B1 | 6/2001 | Gellman et al. | |
| 6,248,088 B1 | 6/2001 | Yoon | |
| 6,451,042 B1 * | 9/2002 | Bonutti | 606/190 |
| 6,554,823 B2 * | 4/2003 | Palmer et al. | 606/1 |
| 6,743,169 B1 * | 6/2004 | Taylor et al. | 600/204 |
| 6,758,809 B2 * | 7/2004 | Briscoe et al. | 600/229 |
| 6,821,247 B2 * | 11/2004 | Vierra et al. | 600/204 |
| 7,025,722 B2 * | 4/2006 | Vierra et al. | 600/204 |
| 2001/0000533 A1 | 4/2001 | Kovac | |
| 2004/0082837 A1 * | 4/2004 | Willis | 600/210 |
| 2004/0143163 A1 * | 7/2004 | Palmer et al. | 600/204 |

FOREIGN PATENT DOCUMENTS

| | | |
|---|---|---|
| DE | 35 42 667 | 6/1986 |
| WO | WO 01/35831 | 5/2001 |
| WO | WO 03/094744 | 11/2003 |

\* cited by examiner

ENDOSCOPIC ORGAN RETRACTOR AND METHOD OF USING THE SAME

CROSS REFERENCE TO RELATED APPLICATIONS

This is a National Stage Application of PCT/US 03/14773 under 35 USC §371(a), which claims the benefit of and priority to U.S. Provisional Patent Application Ser. No. 60/379,327, filed May 9, 2002, the entire contents of which are hereby incorporated by reference.

BACKGROUND

1. Technical Field

The present disclosure relates to devices and methods used for retracting organs and/or body tissue during surgical procedures and, more particularly, to an endoscopic apparatus and methods for retracting or positioning organs and/or body tissue during minimally invasive surgery.

2. Background of Related Art

As a result of the recent technological improvements in surgical instruments, surgical procedures, using minimally invasive techniques, are routinely performed which surgical procedures cause less trauma to the patient. Some minimally invasive surgical procedures have limitations due to the small internal diameter of many commonly used cannulas of trocar systems. As a result, instrument manufacturers must come up with innovative and novel solutions for using many common instruments such as organ retractors and tissue retrieval bags which utilize deformable frame openings to fit through the trocar and into the patient. In fact, some organ retractors and tissue retrieval bags use inflatable frames which form components for manipulating tissue. An exemplary inflatable organ retraction device is disclosed in U.S. Pat. No. 5,823,945 to Moll, et al., the entire content of which is incorporated herein by reference.

As a result thereof, additional systems for pressurizing the inflatable frames are needed. As can be appreciated, inflatable tissue retrieval instruments tend to be vulnerable to accidental deflation in the operating theater and are unnecessarily dependent upon the rigidity of the inflatable structure to support the organ and/or contain the tissue as it is manipulated. Moreover, inflatable type instruments tend to be more complex and costly than corresponding non-inflatable instruments.

Other tissue expanders or retractors are collapsible and can be passed intra-luminally. Such retractors have taken the form of radial fingers which are activatable to extend relative to each other upon entering the body cavity. Exemplary retractors of this type are disclosed in commonly assigned U.S. Pat. Nos. 5,195,505, 5,199,419, 5,381,788 and 5,554,101, the entire contents of each of which are incorporated herein by reference.

Another collapsible retractor structure includes a pair of collapsible fingers joined by a web of resilient material which, upon exposure from a cannula, can expand to form a retractive structure, such as disclosed in U.S. Pat. No. 4,190,042, the entire content of which is incorporated herein by reference.

A need exists for an improved endoscopic organ retractor for passage through reduced diameter cannulas of trocar systems and which are deployable to at least one expanded condition for retracting body organs and tissue.

SUMMARY

According to one aspect of the present disclosure an organ retractor is provided including a shaft having a proximal end and a distal end and defining a longitudinal axis and a longitudinal plane, and at least one organ support assembly operatively coupled to the distal end of the shaft. The organ support assembly includes a plurality of ribs each defining a respective longitudinal axis; the at least one organ support assembly having a first position, in which the longitudinal axis of each of the plurality of ribs is generally parallel with one another, and a second position, in which the longitudinal axis of a first rib of the plurality of ribs is transverse with respect to the longitudinal axis of a second rib of the plurality of ribs; the at least one organ support assembly being pivotable from a first orientation, in which each of the plurality of ribs is generally disposed in the longitudinal plane of the shaft, to a second orientation, in which each of the plurality of ribs is disposed at an angle relative to the longitudinal plane of the shaft, and a support extending between and connected to the first rib and the second rib.

It is envisioned that when the at least one organ support assembly is in the first position, the longitudinal axis of each of the first plurality of ribs is generally parallel with the longitudinal axis of the shaft.

The plurality of ribs can be pivotally connected to one another at a proximal end portion thereof. The at least one organ support assembly is desirably pivotally connected to the distal end of the shaft and arranged so as to permit articulation of the at least one organ support assembly relative to the shaft. The at least one organ support assembly may be pivotally connected to the shaft by a hinge member defines a pivot axis which is oriented substantially orthogonal relative to the longitudinal axis of the shaft.

The organ retractor further desirably includes a deployment and retracting mechanism configured and adapted to urge the at least one organ support assembly from the first position to a plurality of positions including the second position. The deployment and retracting mechanism can be configured and adapted to urge the at least one organ support assembly from the first orientation to a plurality of orientations including the second orientation.

In one embodiment, the deployment and retracting mechanism includes a first rod extending through the shaft and operatively connected to the at least one organ support assembly such that proximal movement of the first rod urges the at least one organ support assembly from the first orientation to one of the plurality of orientations. The deployment and retracting mechanism can further include a second rod extending through the shaft and operatively connected to one of the plurality of ribs such that proximal movement of the second rod urges the at least one organ support assembly from a first position to one of the plurality of positions.

In another embodiment, the deployment and retracting mechanism can include a first cable extending through the shaft and operatively connected to the at least one organ support assembly, arranged so that when the first cable is withdrawn in a proximal direction the at least one organ support assembly is urged from the first position to one of the plurality of positions. The deployment and retracting mechanism can further include a second cable arranged so that when the second cable is withdrawn in a proximal direction the at least one organ support assembly is urged from the first orientation to one of the plurality of orientations.

It is contemplated that the organ retractor further includes a port defining a passageway extending therethrough, wherein the port is configured and adapted to define an opening into a body cavity. Desirably, the shaft and the at least one organ support assembly, when in the first position and in the first orientation, are sized and shaped to be received in the passageway of the port. The port desirably includes a locking mechanism for fixing the position of the shaft relative to the port.

The organ retractor can further include a locking mechanism for securing the position of the retracting and deployment mechanism relative to the shaft to fix the orientation and position of the at least one organ support assembly.

It is envisioned that the organ retractor can further include a handle operatively connected to the proximal end of the shaft.

It is further envisioned that each of the plurality of ribs includes a series of apertures formed therein, the organ retractor further including a vacuum source fluidly connected to the series of apertures formed in each of the plurality of ribs.

It is contemplated that at least one of the plurality of ribs includes a pressure sensor operatively associated therewith.

In one embodiment, at least the distal end of the shaft is longitudinally divided into a first portion and a second portion, wherein a first organ support assembly is operatively connected to a distal end of the first portion and a second organ support assembly is operatively connected to a distal end of the second portion. The first and second portions are pivotally connected to one another so as to be pivotally separatable from one another along the hinge member.

According to another aspect of the present disclosure, the organ retracting system for retracting an organ within a body cavity can include a port defining a passageway extending therethrough, wherein the port is configured and adapted to define an opening into the body cavity and provide access to the organ, and a lifting apparatus configurable to be sized and dimensioned to be received through the passageway of the port. The lifting apparatus includes a shaft having a proximal end and a distal end and defining a longitudinal axis, at least one organ support assembly operatively coupled to the distal end of the shaft, the organ support assembly having a plurality of ribs with a first position substantially aligned with the longitudinal axis of the shaft and at least one second position angled with respect to the longitudinal axis of the shaft, and a support extending between and connected to at least two of the plurality of ribs.

Desirably, the at least one organ support assembly is pivotally connected to the distal end of the shaft so as to define a pivot axis which is orthogonal to the longitudinal axis of the shaft. The lifting apparatus desirably includes a hinge member and at least one organ support assembly is desirably pivotable about the pivot axis of the hinge member.

The plurality of ribs are desirably pivotally connected to one another at a proximal end thereof. Accordingly, the at least one organ support assembly has a first orientation in which the plurality of ribs is substantially disposed in a longitudinal plane of the shaft and at least one second orientation in which at least one of the ribs is angled with respect to the longitudinal plane of the shaft. The plurality of ribs are angled with respect to a plane defined by the longitudinal axis of the shaft and the pivot axis of the hinge member.

According to a further aspect of the present disclosure, a method of retracting an organ in a body cavity during an endoscopic surgical procedure is provided. The method includes the steps of providing an organ retracting system including a port defining a passageway extending therethrough, wherein the port is configured and adapted to define an opening into the body cavity and provide access to the organ and a lifting apparatus configurable to be sized and dimensioned to be received through the passageway of the port. The lifting apparatus includes a shaft having a proximal end and a distal end and defining a longitudinal axis, and at least one organ support assembly operatively coupled to the distal end of the shaft, the organ support assembly having a plurality of ribs each defining a respective longitudinal axis, the at least one organ support assembly having a first position in which the longitudinal axis of each of the plurality of ribs is generally parallel with one another and a second position in which the longitudinal axis of a first rib of the plurality of ribs is transverse with respect to the longitudinal axis of a second rib, the at least one organ support assembly having a support extending between and connected to a first and a second rib of the plurality of ribs.

The method further includes the steps of positioning the port through the surface of the body, passing the at least one organ support assembly, while in the first position, through the passageway of the port, advancing the at least one organ support assembly to a position adjacent the organ to be retracted, manipulating the lifting apparatus to urge the at least one organ support assembly to the second position and positioning the lifting apparatus so that the support extending between the first and second ribs is positioned along the organ, and retracting the organ.

It is envisioned that the at least one organ support assembly has a first orientation in which the plurality of ribs is generally disposed in a longitudinal plane of the shaft and a second orientation in which each of the plurality of ribs is disposed at an angle relative to the longitudinal plane of the shaft, and wherein the step of retracting the organ comprises moving the organ support assembly from the first orientation to the second orientation.

It is contemplated that the step of retracting includes moving the shaft in a proximal direction.

The presently disclosed endoscopic organ retractor and methods, together with attendant advantages, will be best understood by reference to the following detailed description in conjunction with the figures below.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

Preferred embodiments of the presently disclosed organ retractors will now be described in detail with reference to the drawing figures wherein like reference numerals identify similar or identical elements. In the drawings and in the description which follows, the term "proximal", as is traditional, will refer to the end of the surgical device or instrument of the present disclosure which is closest to the operator, while the term "distal" will refer to the end of the device or instrument which is furthest from the operator.

With reference to FIGS. 1-4, an endoscopic organ retractor in accordance with the principles of the present disclosure is shown generally as reference numeral 10. Organ retractor 10 desirably includes a port 20 and a lifting apparatus 40 operatively associated with the port 20. Preferably, the lifting apparatus 40 is selectively couplable with port 20. The lifting apparatus includes a shaft 50 and an organ support assembly 70.

Figure 1:
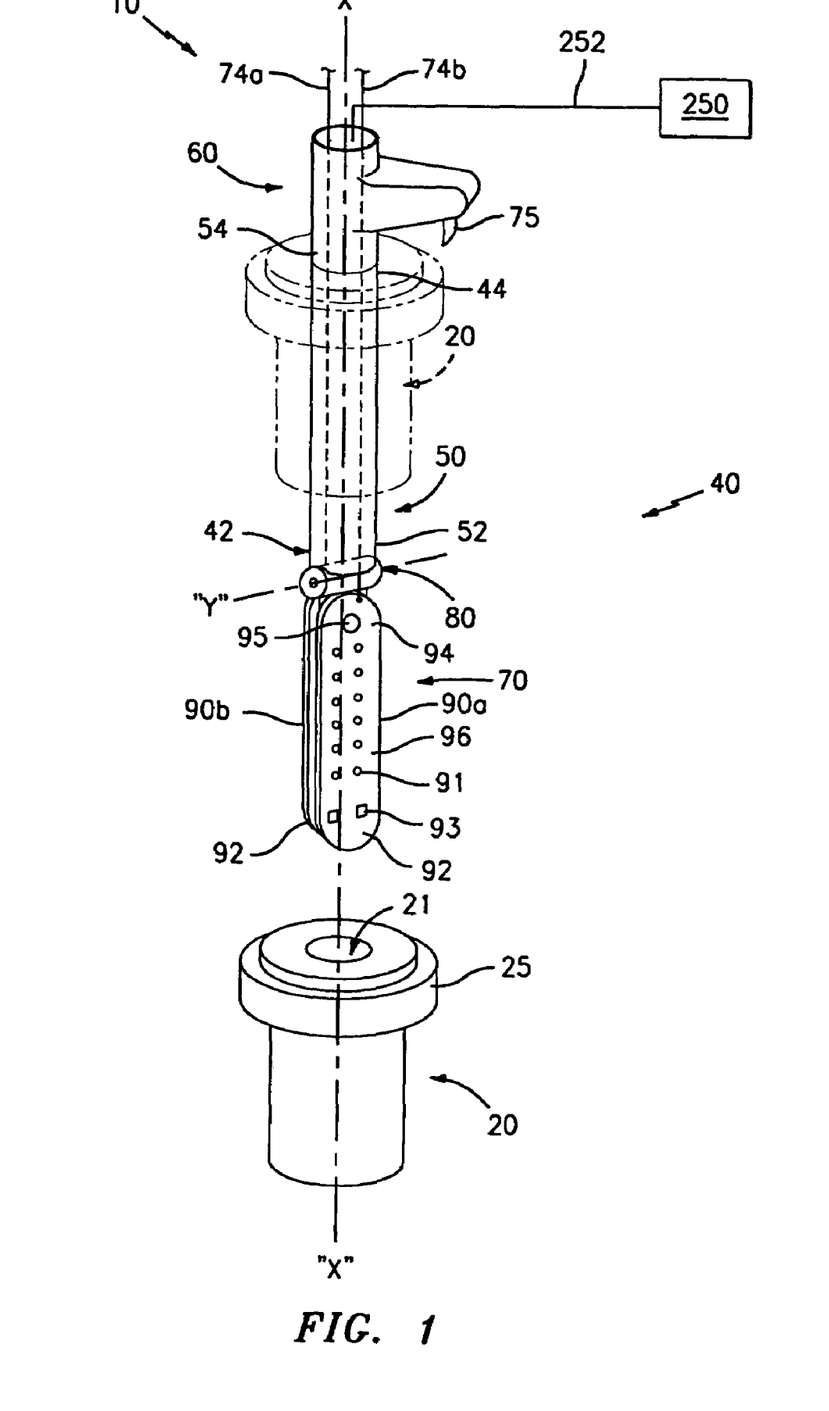
FIG. 1 is a perspective view of an endoscopic organ retractor in accordance with an embodiment of the present invention, shown in a first position.

Port 20 defines a passageway 21 concentric with a central longitudinal axis "X". The port 20 receives the lifting apparatus 40 so that the shaft 50 extends through the port 20. Preferably, lifting apparatus 40 is positioned within passageway 21 of port 20 so as to be longitudinally and rotatably movable therein.

It is contemplated that port 20 can be provided with a locking mechanism 25 which is configured and adapted to selectively control, secure and/or fix the position of lifting apparatus 40 within and/or relative to port 20 along longitudinal axis "X" (i.e., set the depth of lifting apparatus 40). It is further contemplated that locking mechanism 25 can be configured and adapted to selectively control, secure and/or fix the rotational position of lifting apparatus 40 within and/or relative to port 20, depending upon the particular surgical purpose. For example, locking mechanism 25 can be rotated in one direction about longitudinal axis "X", relative to port 20, to thereby constrict passageway 21 to fix the position and orientation of lifting apparatus 40 therein or rotated in the opposite direction to expand passageway 21 and permit movement of lifting apparatus 40 relative to port 20. In certain embodiments, the locking mechanism comprises an apparatus attached to the port 20, or formed integrally therewith, having a housing and a knob rotatably supported in the housing. The housing and the knob include an opening through which the shaft 50 of the lifting apparatus 40 extends. A cylindrical member is coaxially mounted adjacent the knob and also has an opening through which the shaft 50 extends. The knob is either arranged with the housing so that rotation of the knob results in distal movement of the knob, or the knob has structure, such as a flange, for urging the cylindrical member in a distal direction upon rotation of the knob. The cylindrical member is split longitudinally and the housing is arranged so that upon movement of the cylindrical member distally, the cylindrical member engages the housing, and deforms inwardly. The cylindrical member frictionally engages the shaft 50 upon being deformed inwardly, so as to secure the position of the shaft 50.

In further embodiments, the locking mechanism comprises a lever mounted on the port 20, or included in a device that can be attached to the port 20. The lever is accessible by the surgeon and mounted so that upon rotation of the lever, the lever engages the shaft 50, frictionally securing the position of the shaft 50. The locking mechanism may comprise a device disclosed in certain embodiments of U.S. Pat. No. 5,437,645, the disclosure of which is hereby incorporated by reference herein.

It is envisioned that port 20 may include components from trocar systems which facilitate and/or improve sealing and/or insufflation of the body cavity, such as, for example, gaskets, seals, O-rings, duck bills, valves and the like. For example, the port 20 may include a seal for sealing the port 20 in the absence of an instrument therein, such as a duckbill seal, and may also include a further seal that seals around an instrument, such as a resilient material defining an aperture for receiving instruments of various diameters.

As best shown in FIG. 1, shaft 50 has a distal end 42 and a proximal end 44. The organ support assembly 70 is operatively connected to distal end 42 and a handle 60 is operatively connected to proximal end 44. Lifting apparatus 40 is selectively configurable from a first position (see FIG. 1) for passing through passageway 21 of port 20 to at least one second position (see FIG. 2) for retracting organs 200.

Figure 2:
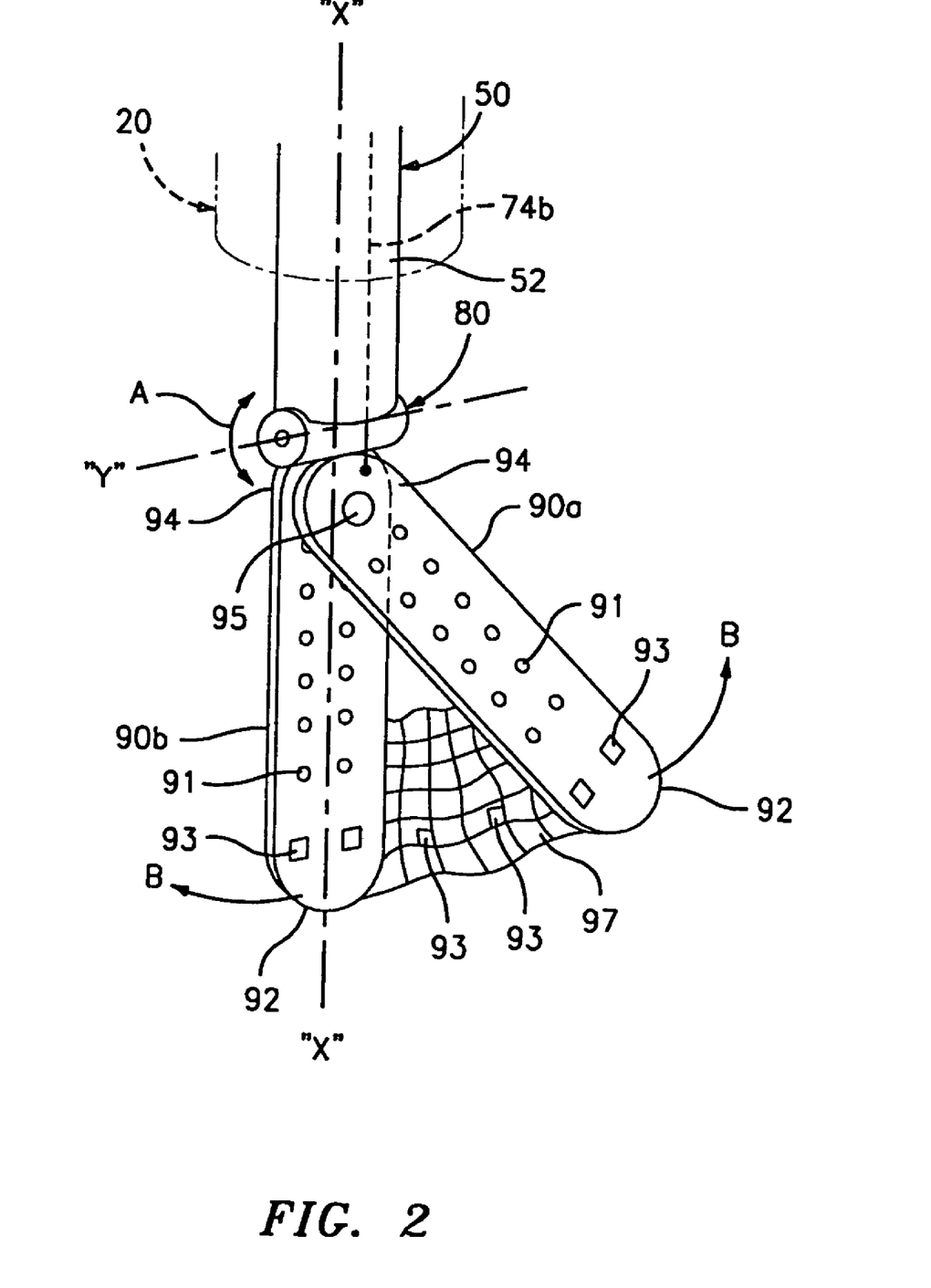
FIG. 2 is a partial perspective view of an organ retractor in accordance with the embodiment of FIG. 1, shown in a second position.

Organ support assembly 70 preferably includes a first elongate rib 90a and a second elongate rib 90b pivotally connected to one another by a pivot pin 95 extending through proximal ends 94 of ribs 90a, 90b. Accordingly, organ support assembly 70 has a first position (see FIG. 1) in which ribs 90a, 90b are in longitudinal alignment with one another and/or interleaved with one another (i.e., distal ends 92 of ribs 90a, 90b are in longitudinal alignment) and a second position (see FIG. 2) in which ribs 90a, 90b are out of longitudinal alignment with one another and/or deployed/fanned-out (i.e., distal ends 92 are spaced from one another). In other words, as seen in FIG. 2, ribs 90a, 90b are configured and adapted to be selectively fanned out in the direction of arrows "B". Desirably, in the first position, ribs 90a, 90b are interleaved, i.e., a longitudinal axis of each of ribs 90a, 90b is in longitudinal alignment with longitudinal axis "X". When in the first position, organ support assembly 70 is more easily inserted and positioned within the body cavity and when in the second position, organ support assembly 70 is configured and adapted to support and/or manipulate organ 200.

Ribs 90a, 90b are desirably fabricated from a medical grade plastic having suitable structural integrity for retracting organ 200 and/or a material having a controlled degree of flexibility or bias to reduce the incidence or possibility of causing damage to organ 200 during retraction and/or manipulation. The ribs 90 may be fabricated from stainless steel, titanium or other medical made materials.

Organ support assembly 70 is preferably pivotally coupled to distal end 42 of shaft 50 via an articulation member 80 to permit articulation of organ support assembly 70 relative to shaft 50. Articulation member 80 is preferably oriented to define a pivot axis "Y" (see FIGS. 1 and 2) which is orthogonal with respect to longitudinal axis "X". Desirably, ribs 90a, 90b are pivotable, about pivot axis "Y" in the direction of arrow "A", from a first orientation in which ribs 90a, 90b are disposed in a plane defined by longitudinal axis "X" and, more particularly by a plane defined by longitudinal axis "X" and pivot axis "Y", to at least one second orientation in which ribs 90a, 90b are disposed in a plane oriented at an angle to the plane defined by longitudinal axis "X" and pivot axis "Y", preferably in a plane generally orthogonal to the pivot axis "Y".

Desirably, when organ support assembly 70 is in the first orientation, in which ribs 90a, 90b are disposed in a plane defined by longitudinal axis "X" and, more particularly by longitudinal axis "X" and pivot axis "Y", and is in the first position, in which ribs 90a, 90b are in longitudinal alignment with one another, lifting apparatus 40 is dimensioned and sized to be introduced through passageway 21 of port 20 and into a body cavity.

Organ support assembly 70 further includes at least one support 97 operatively connected to and extending between ribs 90*a* and 90*b*. The support 97 acts as an additional supporting surface between ribs 90*a*, 90*b* to further support organ 200 during the manipulation and retraction process. The support 97 is preferably configured as a sling-type member fabricated from a mesh-like webbing or material having properties for reducing the incidents of ischemia to organs 200 during retraction by organ support assembly 70. Desirably, an end of support 97 is secured to a juxtaposed surface of a respective rib 90*a*, 90*b* when ribs 90*a*, 90*b* are in the interleaved position. Support 97 is shaped and dimensioned such that when ribs 90*a*, 90*b* are in the fanned out configuration, sling 97 extends therebetween and, preferably has a degree of taughtness for providing support. In certain embodiments, the support or supports are folded in a predetermined manner and enclosed by a sheath. The sheath is desirably arranged to be removed either before or after the lifting apparatus 40 is inserted into the port 20.

Organ retractor 10 further includes a plurality of deployment and retracting members for selectively manipulating organ support assembly 70 from the first orientation to the second orientation and back again, and for selectively manipulating organ support assembly 70 from the first position to the second position and back again. According to one embodiment, as seen in FIG. 2, the shaft 50 desirably defines a passage and deployment and retracting members including a pair of pull/push members or rods 74*a*, 74*b* extend through shaft 50. It is contemplated that a distal end of rod 74*a* is operatively connected to organ support assembly 70 such that when rod 74*a* is pulled in a proximal direction organ support assembly 70 is displaced from the first orientation to the second orientation and when rod 74*a* is pushed in a distal direction organ support assembly 70 is displaced from the second orientation to the first orientation. It is further contemplated that a distal end of rod 74*b* is operatively connected to one or more of ribs 90*a*, 90*b* such that when rod 74*b* is pulled in a proximal direction ribs 90*a*, 90*b* of organ support assembly 70 are displaced from the first position to the second position and when rod 74*b* is pushed in a distal direction ribs 90*a*, 90*b* of organ support assembly 70 are displaced from the second position to the first position.

It is envisioned that the deployment and retracting members can include two sets of pulleys/cables extending through tubular shaft 50. The distal ends of a first set of cables can be operatively connected to organ support assembly 70 to effectuate displacement of organ support assembly 70 from the first orientation to the second orientation and back again. The distal ends of a second set of cables can be operatively connected to one or more of ribs 90*a*, 90*b* to effectuate displacement of ribs 90*a*, 90*b* of organ support assembly 70 from the first position to the second position.

Certain embodiments of U.S. Pat. No. 5,514,157 to Nicholas et al., the entire content of which is incorporated herein by reference disclose a deployment and retracting mechanism for selectively manipulating a retractor from a collapsed to an expanded position and for articulation. Such structure or similar structure can be employed for moving the organ support assembly 70 from the first position to the second position and back again, and for selectively manipulating organ support assembly 70 from the first orientation to the second orientation and back again. Certain embodiments of U.S. Pat. Nos. 5,271,385 and 5,195,505, the disclosures of which are hereby incorporated by reference herein, disclosure further deployment and retracting mechanisms which may be used.

It is envisioned that any combination of rods, cables or other structure known in the art can be used in cooperation with one another to effectuate the displacement of organ support assembly 70 from the first orientation and position to a second orientation and position and back again.

Organ retractor 10 desirably further includes a locking mechanism 75 configured and adapted to fix the position and/or orientation of organ support assembly 70. It is envisioned that locking mechanism 75 can be operatively associated with handle 60 and be configured and adapted such that rods 74*a*, 74*b* are operatively engaged therewith. Locking mechanism 75 can have a first position in which rods 74*a*, 74*b* are free to be displaced distally and proximally and at least one other position in which at least one of rods 74*a*, 74*b* are fixed in position relative to shaft 50. In particular, locking mechanism 75 can fix the position of rod 74*a* to maintain organ support assembly 70 in an angled orientation relative to longitudinal axis "X" and fix the position of rod 74*b* to maintain organ support assembly 70 in the second position (i.e., ribs 90*a*, 90*b* are fanned out). A locking mechanism may also be used with a cable or any other deployment and retracting mechanism. In certain embodiments, the locking mechanism 75 is configured similarly to the locking mechanism 25 for securing the position of the lifting apparatus with respect to the axis X. The locking mechanism may comprise a movable latch accessible to the surgeon and rotatably mounted on a proximal end of the shaft 50 so that upon rotation of the latch, the latch frictionally engages the rod 74*a*, rod 74*b* or both. Such a latch may also be used with a cable or other deployment and retracting mechanism. In addition, the locking mechanism may comprise a deformable collar or other member for engaging one or more rods or cables and frictionally securing the position of the deployment and retracting mechanism.

Figure 3:
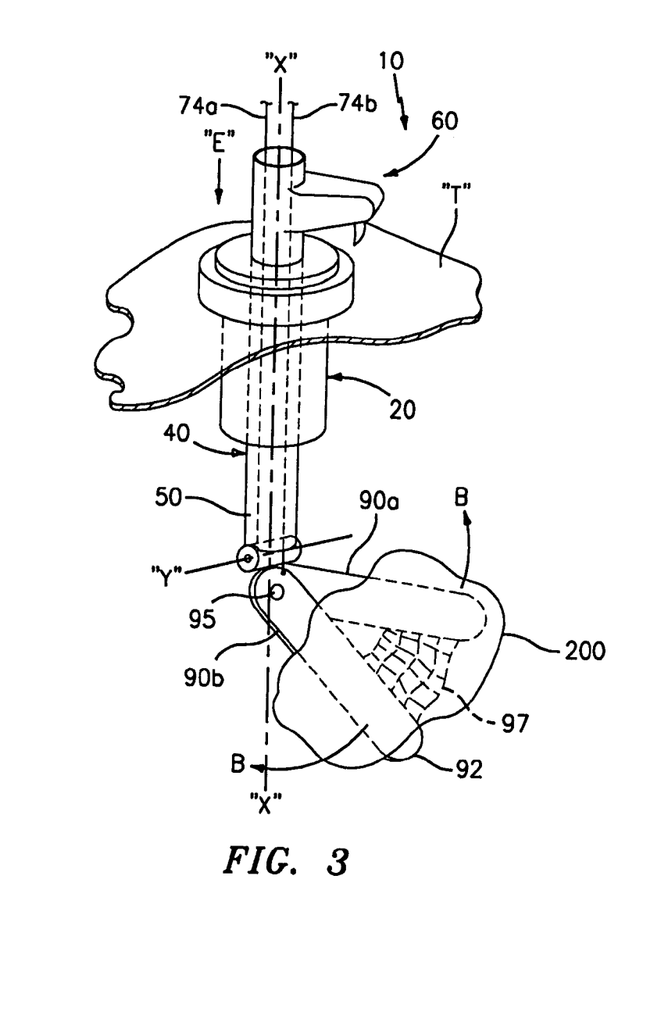
FIG. 3 is a perspective view of an organ retractor in accordance with the embodiment of FIGS. 1-2, shown in the second position.
Figure 4:
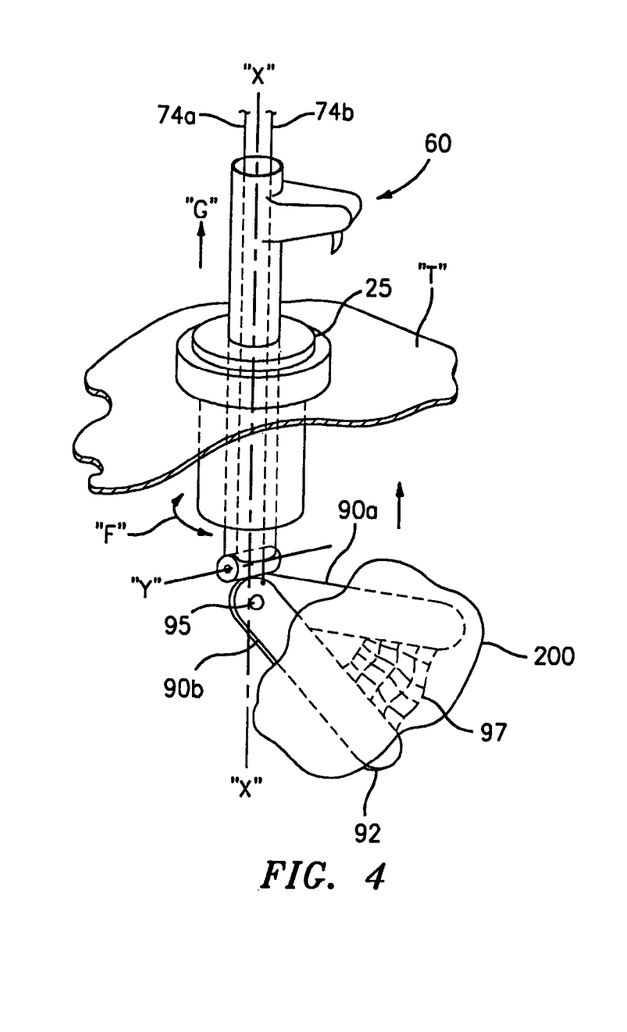
FIG. 4 is a perspective view of an organ retractor in accordance with the embodiment of FIGS. 1-3, shown in a third position.

With reference to FIGS. 1-4 and, in particular, FIGS. 3 and 4, use and operation of organ retractor 10 will now be described. Initially, as is known in the art, a trocaris inserted through body tissue "T" of the patient, in the direction of arrow "E" to create an opening in the surface of body tissue "T" and to provide access to interior organs of the patient and to the operating cavity. The operating cavity is then insufflated to facilitate viewing of the operating cavity and the internal organ.

In use, port 20 is positioned to extend through an opening (not shown) formed in the surface of body tissue "T" such that passageway 21 defines a lumen extending through body tissue "T". With port 20 in position, lifting apparatus 40 is introduced into the body cavity through port 20. In particular, with organ support assembly 70 in the first position and in the first orientation, lifting apparatus 40 is inserted and advanced into the body cavity through passageway 21 of port 20 at least until distal end 52 of shaft 50 extends beyond the distal-most end of port 20 (i.e., ribs 90*a*, 90*b* and hinge-like member 80 are positioned distally of the distal-most end of port 20.

Lifting apparatus 40 is desirably manipulated by the surgeon such that organ support assembly 70 is positioned proximate organ 200 which is desired to be retracted. With organ support assembly 70 so positioned, ribs 90*a*, 90*b* are fanned out, as described above. In particular, organ support assembly 70 is urged to the second position by manipulating the pulling rod 74*b* in a proximal direction to thereby separate distal ends 92 of ribs 90*a*; 90*b* from one another and deploy sling 97.

With organ support assembly 70 in the second position, the surgeon can move organ support assembly 70 from the first orientation to the second orientation to retract organ 200. The organ support assembly 70 is urged to the second orientation by pulling rod 74*a* in a proximal direction to thereby pivot organ support mechanism about pivot axis "Y" in the direction of organ 200 and thereby retract organ 200. Additionally or alternatively, the surgeon can move shaft 50 in a proximal direction to retract the organ.

Alternatively, as seen in FIGS. 3 and 4, lifting apparatus 40 is distally advanced through port 20 until organ support assembly 70 is positioned beyond organ 200 to be retracted. Organ support assembly 70 is then urged to the second position to deploy ribs 90*a*, 90*b* and then urged to the second orientation to approximate ribs 90*a*, 90*b* and sling 97 to organ 200. With organ support mechanism 200 positioned toward organ 200, lifting apparatus 40 is withdrawn through port 20 in a proximal direction, as indicated by arrow "G" of FIG. 4 to thereby retract and/or lift organ 200 in direction "G".

If needed, the surgeon can rotate lifting apparatus 40, about longitudinal axis "X", relative to port 20, in the directions indicated by double headed arrow "F". By so doing, organ 200 can be urged to either the left or the right as needed.

In certain preferred embodiments, the lifting apparatus 40 can be locked in position relative to port 20 after retracting an organ by engaging locking mechanism 25 of port 20. In this manner, lifting apparatus 40 can be maintained in a retracted position during the length of the surgical procedure thereby freeing at least one hand of the surgeon and/or other user to perform other functions. A support structure may be engaged with port 20 and the operating table or other surfaces for further supporting the lifting apparatus 40. Such structures are known in the art.

Upon completion of the surgical procedure, lifting apparatus 40 can be withdrawn from the surgical site by disengaging locking mechanism 25, returning organ 200 substantially into its normal corporal position, urging organ support assembly 70 to its first orientation and its first position, and withdrawing lifting apparatus in a proximal direction.

As seen in FIGS. 1 and 2, it is contemplated that each rib 90*a*, 90*b* can be provided with at least one, preferably a series of apertures 91 formed along the surface thereof. It is envisioned that apertures 91 are in fluid communication with an internal or an external source of vacuum 250 via a series of conduits 252. In use, source of vacuum 250 can activated to transmit a vacuum to each aperture 91 to thereby enhance the gripping ability of each rib 90*a*, 90*b* with organ 200. The apertures 91 are desirably shaped so as to control the forces on the organ 20.

It is further contemplated that organ retractor 10 can include a pressure sensing system wherein each rib 90*a*, 90*b* and/or support 97 can include at least one sensor, such as, for example, a pressure sensor 93 which is configured to provide feedback regarding the forces on the organ to the surgeon during retraction of organ 200. For example, pressure sensors 93 may be positioned at different locations along the surface of ribs 90*a*, 90*b* and sling 97 to provide accurate feedback regarding the retractive pressure being applied to organ 200. The output of pressure sensors 93 can be readily integrated to provide a continuous feedback to the surgeon on the amount of pressure being applied to organ 200 by lifting apparatus 40. Pressure sensors 93 can be connected to caution and/or warning systems which provide audible, visual and/or tactile signals to the surgeon to indicate changes of pressure sensed. The pressure sensor may be connected to a display and/or computer system for receiving data from the sensors and displaying such data in a visual format.

The pressure sensing system can also provide the status of the grip of lifting apparatus 40 on organ 200. For example, if lifting apparatus 40 begins to lose grip of organ 200, the pressure sensing system can detect the loss/change of pressure and inform the surgeon. Likewise, the pressure sensing system can provide cautionary notice when the position or tightness of the grip on organ 200, by lifting apparatus 40, has produced excessive pressure points in order to reduce the forces on organ 200 during the retracting and/or lifting process.

It is further envisioned that portions of support 97 and/or ribs 90*a*, 90*b* can be at least partially inflatable. The inflatable portions (not shown) can be in fluid communication with source of fluid 250.

Figure 5:
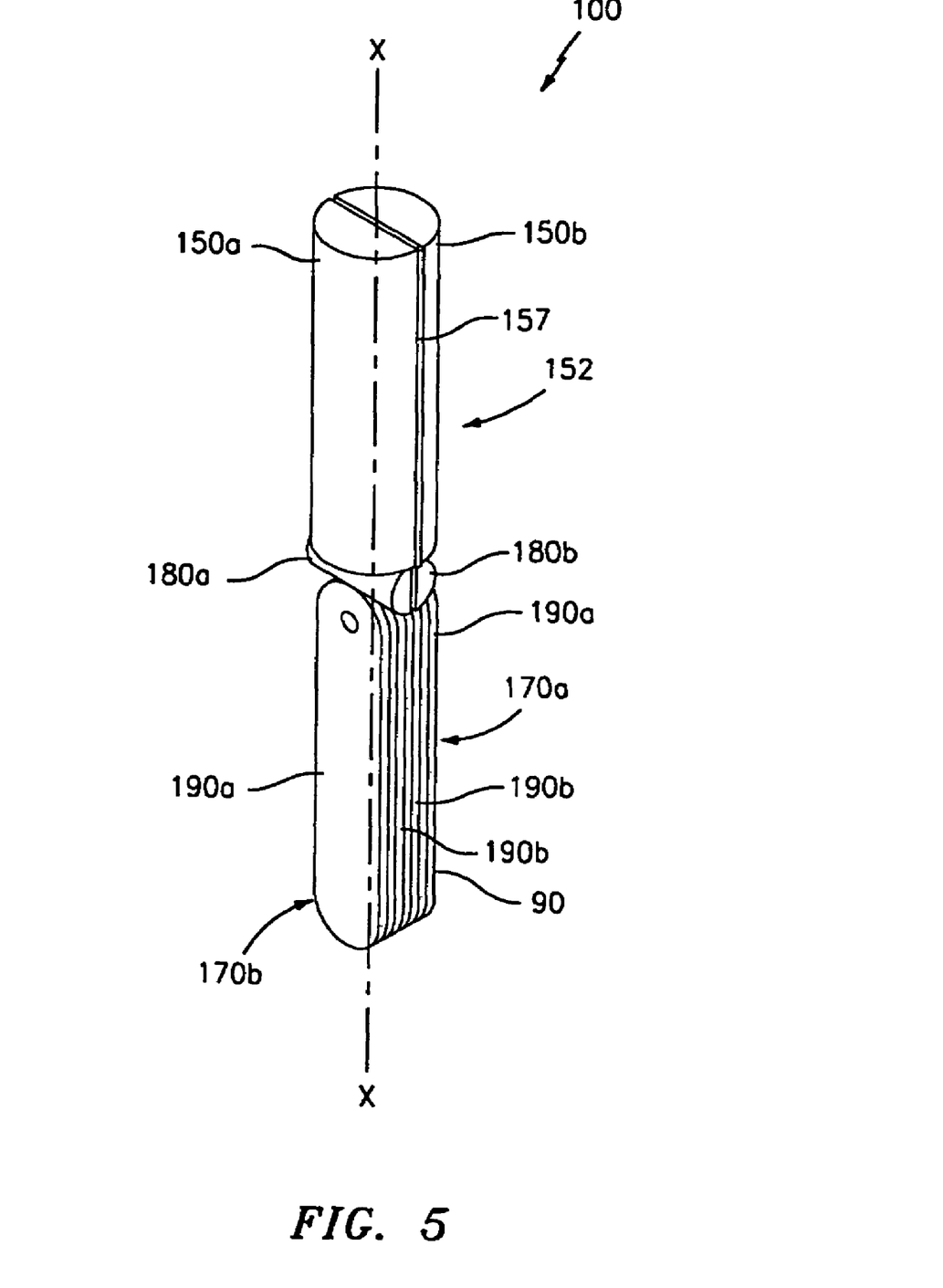
FIG. 5 is a perspective view of an endoscopic organ retractor according to another embodiment of the present invention, shown in a first position.
Figure 6:
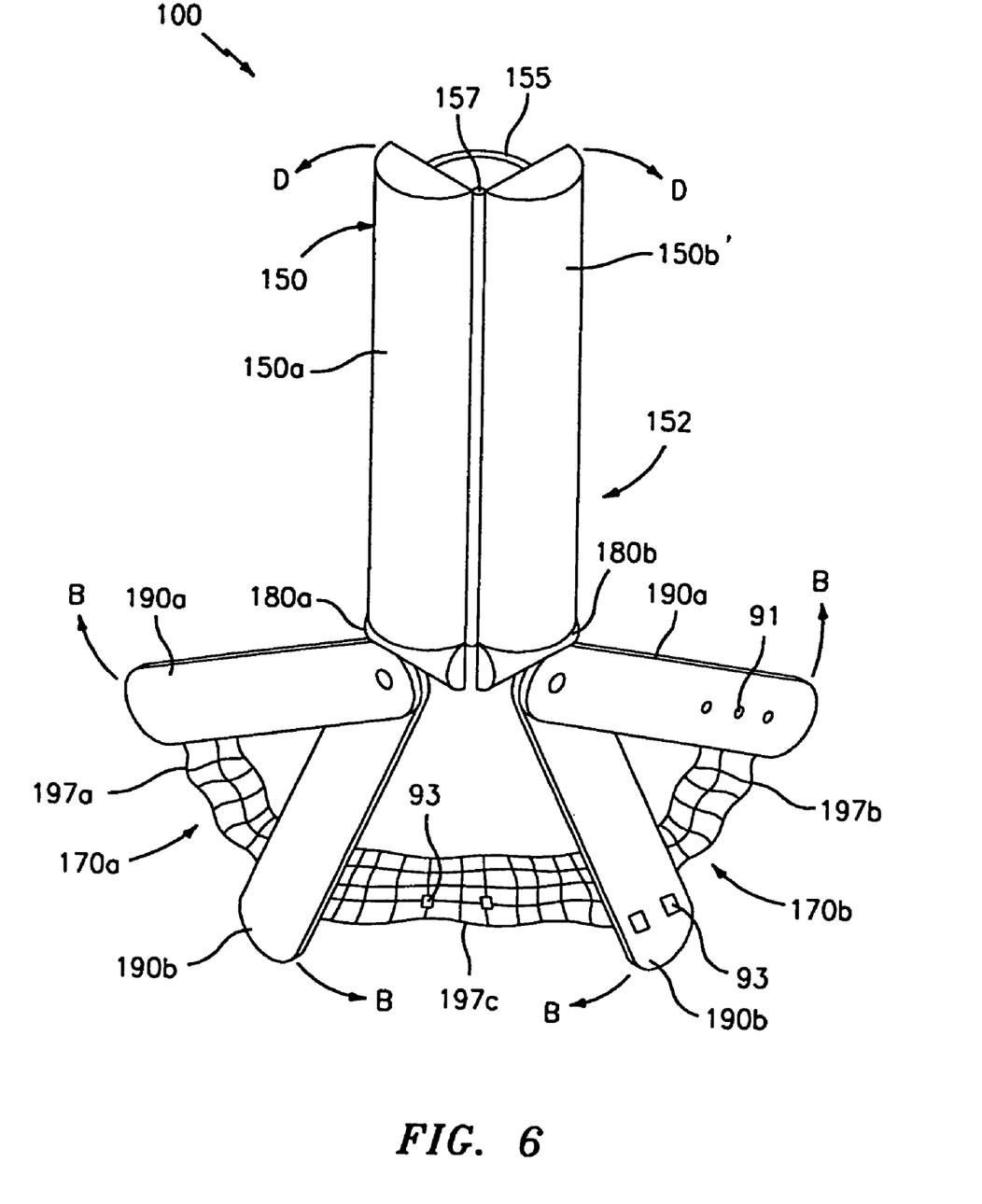
FIG. 6 is a partial perspective view of an organ retractor in accordance with the embodiment of FIG. 5 shown in a second position.

Turning now to FIGS. 5 and 6, an organ retractor in accordance with an alternate embodiment of the present disclosure is shown generally as 100. As seen in FIGS. 5 and 6, distal end portion 152 of tubular shaft 150 is longitudinally divided into a first and a second semi-circular shaft 150*a* and 150*b*, respectively. Semi-circular shafts 150*a*, 150*b* are connected to one another by a longitudinally aligned hinge-like member 157. Each semi-circular shaft 150*a*, 150*b* includes a respective organ support assembly 170*a*, 170*b* operatively coupled to a distal end thereof via a respective hinge-like member 180*a*, 180*b*. Preferably, organ support assemblies 170*a*, 170*b* are operatively coupled to respective semi-circular shafts 150*a*, 150*b*, in the same manner by which organ support assembly 70 is coupled to shaft 50 of organ retractor 10.

Organ retractor 100 preferably includes a first support 197*a* interconnecting and extending between ribs 190*a*, 190*b* of organ support assembly 170*a*, a second support 197*b* interconnecting and extending between ribs 190*a*, 190*b* of organ support assembly 170*b*, and a third support 197*c* extending between and interconnecting rib 190*b* of organ support assembly 170*a* and rib 190*b* of organ support assembly 170*b*. Supports 197*a*-197*c* are preferably used to further support organ 200 during the retracting and/or lifting procedure.

In use, with port 20 positioned to extend through body tissue 'T', organ retractor 100 is arranged in a first longitudinally-aligned configuration for passage through passageway 21 of port 20. In particular, as seen in FIG. 5, organ support assemblies 170*a*, 170*b* are interleaved, each organ support assembly 170*a*, 170*b* is longitudinally aligned with longitudinal axis "X", and semi-circular shafts 150*a*, 150*b* are approximated towards one another such that hinge-like members 180*a*, 180*b* are adjacent and parallel to one another.

After organ support assemblies 170*a*, 170*b* are passed through-port 20, organ support assemblies 170*a*, 170*b* are pivotally separated from one another along hinge 157, as indicated by arrows "D" and desirably fixed in the open position at a desired degree of angular separation. It is contemplated that hinge 157 can accommodate rotating organ support assemblies 170*a*, 170*b* up to approximately 180 degrees relative to one another. Hinge 157 may also include a locking mechanism 155 which cooperates with a handle at the proximal end of the apparatus and semi-circular shafts 150*a*, 150*b* to lock hinge-like members 180*a*, 180*b* and/or lock organ support assemblies 170*a*, 170*b* at various angular relationships depending upon a particular purpose. As can be appreciated, this enables independent or conjunctive movement of organ support assemblies 170*a*, 170*b* by the combination of hinge 157 and hinge-like members 180*a*, 180*b* which facilitates lifting organ 200. In certain embodiments, the ribs 190 may also be arranged to fan-out as discussed above in connection with FIGS. 1 and 2.

Organ support assemblies 170*a*, 170*b* are positioned adjacent organ 200. Organ support assemblies 170*a*, 170*b* are then each urged, as described above with regard to organ retractor 100, from the first orientation to the second orientation, to retract organ 200. Ribs 190*a*, 190*b* of organ support assemblies 170*a*, 170*b* are desirably fanned out (i.e., organ support assemblies are urged to their second position) such that supports 197a-197c are extended to span across and further support organ 200 during the retracting and/or lifting procedure.

A locking mechanism (as discussed above in connection with FIG. 1) can then be engaged to fix the position of and/or orientation organ support assemblies 170a, 170b. Lifting apparatus 140 can be translated and/or rotated as needed to further retract/manipulate/cradle organ 200. A further locking mechanism is desirably included on port 20 (as discussed above in connection with FIGS. 1 and 2) to fix the depth and/or rotational position of lifting apparatus 140 relative to the port.

To replace organ 200 upon completion of the surgical procedure, the locking mechanisms are manipulated and/or disengaged to allow organ 200 to gradually return to its original position within the opening cavity. Lifting apparatus 140 is then collapsed for subsequent withdrawal through port 20.

It is envisioned that the outer surface of shaft 50 can be provided with a series of longitudinally extending indicia (not shown) thereon, preferably in the form of a measurement scale. In this manner, when lifting apparatus 40 is inserted through passageway 21 of port 20, the depth of organ support assembly 70 (i.e., the amount of lifting apparatus 40) extending into the body cavity of the patient can be readily ascertained by the surgeon. Moreover, the surgeon can readily ascertain the distance and/or amount organ 200 has been retracted. It is further envisioned that the outer surface of shaft 50 can include a single mark or indicia (not shown) thereon which indicated to the surgeon the direction in which organ support assembly 70 is pivotable.

Although the illustrative embodiments of the present disclosure have been described herein, it is to be understood that the disclosure is not limited to those precise embodiments, and that various other changes and modifications may be affected therein by one skilled in the art without departing from the scope or spirit of the disclosure. All such changes and modifications are intended to be included within the scope of the disclosure. For example, two or more organ support assemblies may be provided and the shaft may be divided into two or more parts. Apparatus according to embodiments of the present invention includes multiple support assemblies with or without supports extending between ribs. The ribs may comprise paddles or other shapes. Embodiments of the invention include ribs that fan-out with or without articulation. Apparatus according to the present invention include a lifting apparatus with or without a port.

What is claimed is:

1. An organ retractor, comprising:
    a shaft having a proximal end and a distal end and defining a longitudinal axis and a longitudinal plane; and
    at least one organ support assembly operatively coupled to the distal end of the shaft, the organ support assembly including:
        a plurality of ribs each defining a respective longitudinal axis, wherein each rib is cantilevered so as to be supported only at a proximal end and to have a free distal end; the at least one organ support assembly having a first position, in which the longitudinal axis of each of the plurality of ribs is generally parallel with one another, and a second position, in which the longitudinal axis of a first rib of the plurality of ribs is transverse with respect to the longitudinal axis of a second rib of the plurality of ribs; the at least one organ support assembly being pivotable from a first orientation, in which each of the plurality of ribs is generally disposed in the longitudinal plane of the shaft, to a second orientation, in which each of the plurality of ribs is disposed at an angle relative to the longitudinal plane of the shaft, wherein the plurality of ribs are pivotally connected to one another at a proximal end portion thereof;
        a sling extending between and connected to the first rib and the second rib; and
    a deployment and retracting mechanism configured and adapted to urge the at least one organ support assembly from the first position to a plurality of positions including the second position and from the first orientation to a plurality of orientations including the second orientation, the deployment and retracting mechanism including a first rod extending through the shaft and operatively connected to the at least one organ support assembly such that proximal movement of the first rod urges the at least one organ support assembly from the first orientation to one of the plurality of orientations and a second rod extending through the shaft and operatively connected to one of the plurality of ribs such that proximal movement of the second rod urges the at least one organ support assembly from a first position to one of the plurality of positions;
    wherein when the at least one organ support assembly is in the first position, the longitudinal axis of each of the first plurality of ribs is generally-parallel with the longitudinal axis of the shaft; and
    wherein the at least one organ support assembly is pivotally connected to the distal end of the shaft and arranged so as to permit articulation of the at least one organ support assembly relative to the shaft.

2. The organ retractor according to claim 1, wherein the organ support assembly is pivotally connected to the distal end of the shaft by a hinge member defining a pivot axis which is oriented substantially orthogonal relative to the longitudinal axis of the shaft.

3. The organ retractor according to claim 1, wherein the deployment and retracting mechanism includes a first cable extending through the shaft and operatively connected to the at least one organ support assembly, arranged so that when the first cable is withdrawn in a proximal direction the at least one organ support assembly is urged from the first position to one of the plurality of positions.

4. An organ retractor comprising:
    a shaft having a proximal end and a distal end and defining a longitudinal axis and a longitudinal plane; and
    at least one organ support assembly operatively coupled to the distal end of the shaft, the organ support assembly including:
        a plurality of ribs each defining a respective longitudinal axis, wherein each rib is cantilevered so as to be supported only at a proximal end and to have a free distal end; the at least one organ support assembly having a first position, in which the longitudinal axis of each of the plurality of ribs is generally parallel with one another, and a second position, in which the longitudinal axis of a first rib of the plurality of ribs is transverse with respect to the longitudinal axis of a second rib of the plurality of ribs; the at least one organ support assembly being pivotable from a first orientation, in which each of the plurality of ribs is generally disposed in the longitudinal plane of the shaft, to a second orientation, in which each of the plurality of ribs is disposed at an angle relative to the longitudinal plane of the shaft, wherein the plurality of ribs are pivotally connected to one another at a proximal end portion thereof;

a sling extending between and connected to the first rib and the second rib; and a deployment and retracting mechanism configured and adapted to urge the at least one organ support assembly from the first position to a plurality of positions including the second position, wherein the deployment and retracting mechanism includes a first cable extending through the shaft and operatively connected to the at least one organ support assembly, arranged so that when the first cable is withdrawn in a proximal direction the at least one organ support assembly is urged from the first position to one of the plurality of positions and a second cable arranged so that when the second cable is withdrawn in a proximal direction the at least one organ support assembly is urged from the first orientation to one of the plurality of orientations;

wherein when the at least one organ support assembly is in the first position, the longitudinal axis of each of the first plurality of ribs is generally-parallel with the longitudinal axis of the shaft; and wherein the at least one organ support assembly is pivotally connected to the distal end of the shaft and arranged so as to permit articulation of the at least one organ support assembly relative to the shaft.

5. The organ retractor according to claim 1, further including a port defining a passageway extending therethrough, wherein the port is configured and adapted to define an opening into a body cavity.

6. The organ retractor according to claim 5, wherein the shaft and the at least one organ support assembly, when in the first position and in the first orientation, are sized and shaped to be received in the passageway of the port.

7. The organ retractor according to claim 6, wherein the port further includes a locking mechanism for fixing the position of the shaft relative to the port.

8. The organ retractor according to claim 1, further comprising a locking mechanism for securing the position of the retracting and deployment mechanism relative to the shaft to fix the orientation and position of the at least one organ support assembly.

9. The organ retractor according to claim 1, further including a handle operatively connected to the proximal end of the shaft.

10. The organ retractor according to claim 1, wherein each of the plurality of ribs includes a series of apertures formed therein, the organ retractor further including a vacuum source fluidly connected to the series of apertures formed in each of the plurality of ribs.

11. The organ retractor according to claim 1, wherein at least one of the plurality of ribs includes a pressure sensor operatively associated therewith.

12. An organ retractor comprising:
a shaft having a proximal end and a distal end and defining a longitudinal axis and a longitudinal plane; and
at least one organ support assembly operatively coupled to the distal end of the shaft, the organ support assembly including:
a plurality of ribs each defining a respective longitudinal axis, wherein each rib is cantilevered so as to be supported only at a proximal end and to have a free distal end; the at least one organ support assembly having a first position, in which the longitudinal axis of each of the plurality of ribs is generally parallel with one another, and a second position, in which the longitudinal axis of a first rib of the plurality of ribs is transverse with respect to the longitudinal axis of a second rib of the plurality of ribs; the at least one organ support assembly being pivotable from a first orientation, in which each of the plurality of ribs is generally disposed in the longitudinal plane of the shaft, to a second orientation, in which each of the plurality of ribs is disposed at an angle relative to the longitudinal plane of the shaft; and
a sling extending between and connected to the first rib and the second rib;
wherein at least the distal end of the shaft is longitudinally divided into a first portion and a second portion, wherein a first organ support assembly is operatively connected to a distal end of the first portion and a second organ support assembly is operatively connected to a distal end of the second portion.

13. The organ retractor according to claim 12, wherein the first and second portions are pivotally connected to one another so as to be pivotally separatable from one another.

* * * * *